United States Patent [19]

Pedersen

[11] 4,206,763
[45] Jun. 10, 1980

[54] ULTRASONIC SCANNER FOR BREAST CANCER EXAMINATION

[75] Inventor: Peder C. Pedersen, Darby, Pa.

[73] Assignee: Drexel University, Philadelphia, Pa.

[21] Appl. No.: 929,982

[22] Filed: Aug. 1, 1978

[51] Int. Cl.$^2$ ............................................. A61B 10/00
[52] U.S. Cl. ..................................... 128/660; 73/633
[58] Field of Search .................... 128/2 V, 24 A, 660; 73/644, 67.5 R, 67.6, 633, 71.5 US, 640

[56] References Cited

U.S. PATENT DOCUMENTS

| | | | |
|---|---|---|---|
| 3,688,564 | 9/1972 | McDicken | 128/2 V |
| 3,765,403 | 10/1973 | Brenden | 128/2 V |
| 4,130,112 | 12/1978 | Frazer | 128/2 V |

*Primary Examiner*—Willis Little
*Attorney, Agent, or Firm*—Paul & Paul

[57] ABSTRACT

Ultrasonic examination for carcinoma of the breast is accomplished rapidly and reliably by the method and apparatus disclosed herein. The apparatus is comprised of a compartment in which water is drawn upward, by suction, over the breast being examined, and in which an ultrasonic transducer revolves around the breast to obtain complete 360° scans. The patient can be seated in a comfortable position during the examination, and the total time required for examination in an asymptomatic case is estimated to be less than five minutes. The suction holds the breast in place, and there is no need for a membrane to cover the breast, thus improving the accuracy of the test. Various cross-sectional images of the breast may be generated by a conventional two-dimensional B-mode scanning technique.

18 Claims, 5 Drawing Figures

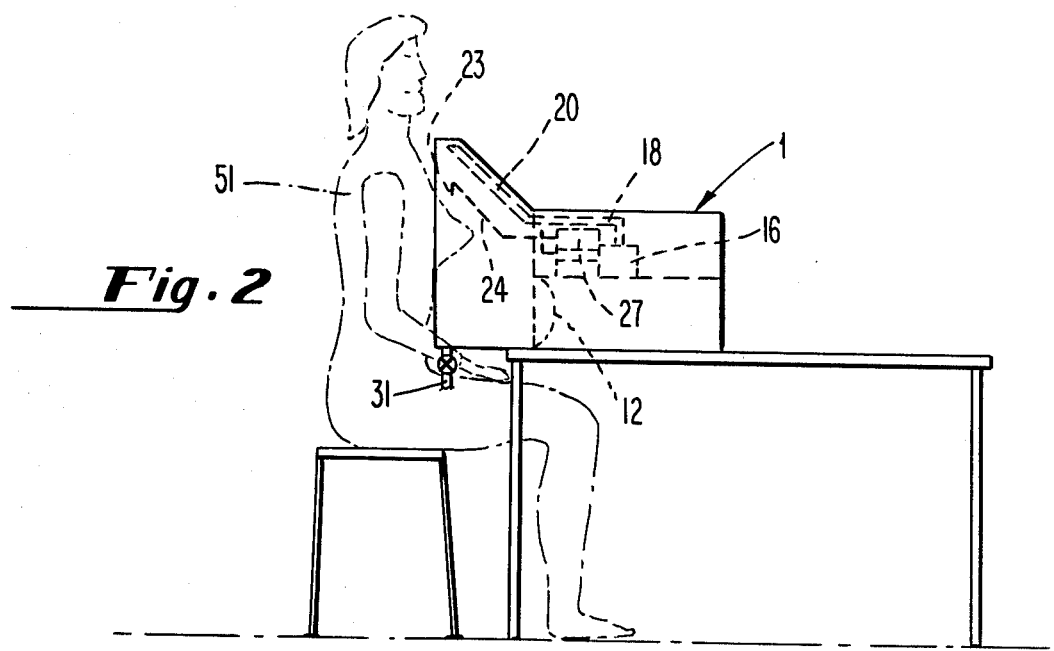

ULTRASONIC SCANNER FOR BREAST CANCER EXAMINATION

BACKGROUND OF THE INVENTION

This invention relates to breast cancer examination by ultrasonic scanning techniques and, in particular, discloses a new method and apparatus for safe and efficient detection of this disease. Carcinoma of the breast is the major cause of death from cancer in women, taking the lives of about 27,000 women in the United States every year. While the five-year survival rate for breast cancer revealed by self-examination is 45–55%, the use of early detection methods can give survival rates in the range of 80–85%. Currently, a controversy exists in the medical community regarding the desirability of mammography as a screening procedure because it has been claimed that the diagnostic advantages of mammography may be outweighed by the risk of inducing cancer by the procedure itself. Thus there is a need for development of alternative methods of early cancer detection.

One of these alternative methods is ultrasonic scanning of the breast by pulse-echo technique. This method basically involves directing short pulses of high-frequency sound energy at the breast followed by the detection of reflected waves. Reflection of the waves occurs at boundaries between the media through which the waves travel. Thus, reflection occurs at the interfaces between skin and fat tissue, or between the skin and the surrounding external medium. The presence of a tumor within the breast establishes such boundaries and the tumor will therefore be detectable from the reflection of ultrasonic waves. When the reflected waves (echoes) are displayed on a conventional B-scope, an outline of the boundary of the tumor will appear on the display. Differentiation between solid and cystic masses may be obtained by a high gain setting in which case a solid mass will appear as a bright area whereas a cystic mass will appear as a dark (echo-free) area, because the fluid in the cyst is essentially transparent to acoustic energy.

Various ultrasonic scanning techniques are presently employed for breast cancer examination, but several drawbacks remain. In typical applications of this method, the woman being examined lies in a prone position with one breast immersed in a water bath and with the ultrasonic transducer scanning in a horizontal plane. Other techniques used require the patient to lie on her back during the test. These methods are cumbersome, and are not suited for mass screening. Also, the use of methods currently available often leads to deformation of the breast or to movement of the breast during scanning, resulting in inaccuracy and poor reproducibility.

SUMMARY OF THE INVENTION

The present invention provides an apparatus for breast cancer examination which substantially reduces the problems described above. The invention comprises a water bath compartment having a cushioned hole into which a breast is inserted. Water is stored in a collapsible bag compartment, and is allowed to flow freely into the water bath compartment. An evacuation pump draws air out of the water bath compartment, thereby drawing water upward out of the collapsible bag compartment, and also firmly pulling the breast into the water bath compartment. After the breast is completely submerged in water, an ultrasonic transducer scans the breast in various planes and with various orientations. The breast is imaged by known imaging techniques, e.g. the pulse-echo technique, and is displayed or recorded as a two-dimensional cross-sectional image.

The method described herein is safe, efficient, and rapid. The patient may sit in a comfortable position during the examination, which is estimated to last about 90 seconds per breast. The fact that the breast is in direct contact with water, in the water bath compartment, enables the test to be performed with considerable accuracy, because there is no membrane or other intermediate material to interfere with the transmission and reflection of ultrasonic waves.

Accordingly, it is a primary object of the present invention to provide a safe and efficient apparatus for breast cancer examination by ultrasonic scanning.

It is a further object of the present invention to provide an apparatus as described above, wherein the patient can be seated in a comfortable position during the examination.

It is a further object of the present invention to provide an apparatus as described above, wherein the total examination time is usually less than five minutes.

It is a further object of the present invention to provide an apparatus for breast cancer examination wherein no support for the breast is necessary during the examination.

It is a further object of the present invention to provide an apparatus as described above, wherein the breast is not deformed during examination.

It is a further object of the present invention to provide an apparatus as described above, wherein the apparatus is capable of producing a high-quality, 360° scan.

It is a further object of the present invention to provide an apparatus as described above, wherein the scans can be performed with a high degree of reproducibility.

It is a further object of the present invention to provide an apparatus for breast cancer examination which requires little training to operate.

It is a further object of the present invention to provide an apparatus as described above, wherein the apparatus is adaptable for use with conventional ultrasonic display means.

It is a further object of the present invention to provide a relatively simple but accurate method of breast cancer examination.

Other objects and advantages of the present invention will be apparent to those skilled in the art from a reading of the following brief description of the drawings, the detailed description of the invention, and the appended claims.

BRIEF DESCRIPTION OF THE DRAWINGS

FIG. 2 is a side elevational view of the scanner, illustrating the position assumed by the woman undergoing the examination.

FIG. 3a is a partially schematic side elevational view of the scanner, illustrating the apparatus before the examination procedure has begun.

FIG. 3b is a view similar to that of FIG. 3a, illustrating the drawing of the water upward and over the breast.

FIG. 3c is a view similar to that of FIG. 3a, illustrating the actual ultrasonic scanning procedure through the use of a moving transducer.

DETAILED DESCRIPTION OF THE INVENTION

Figure 1:
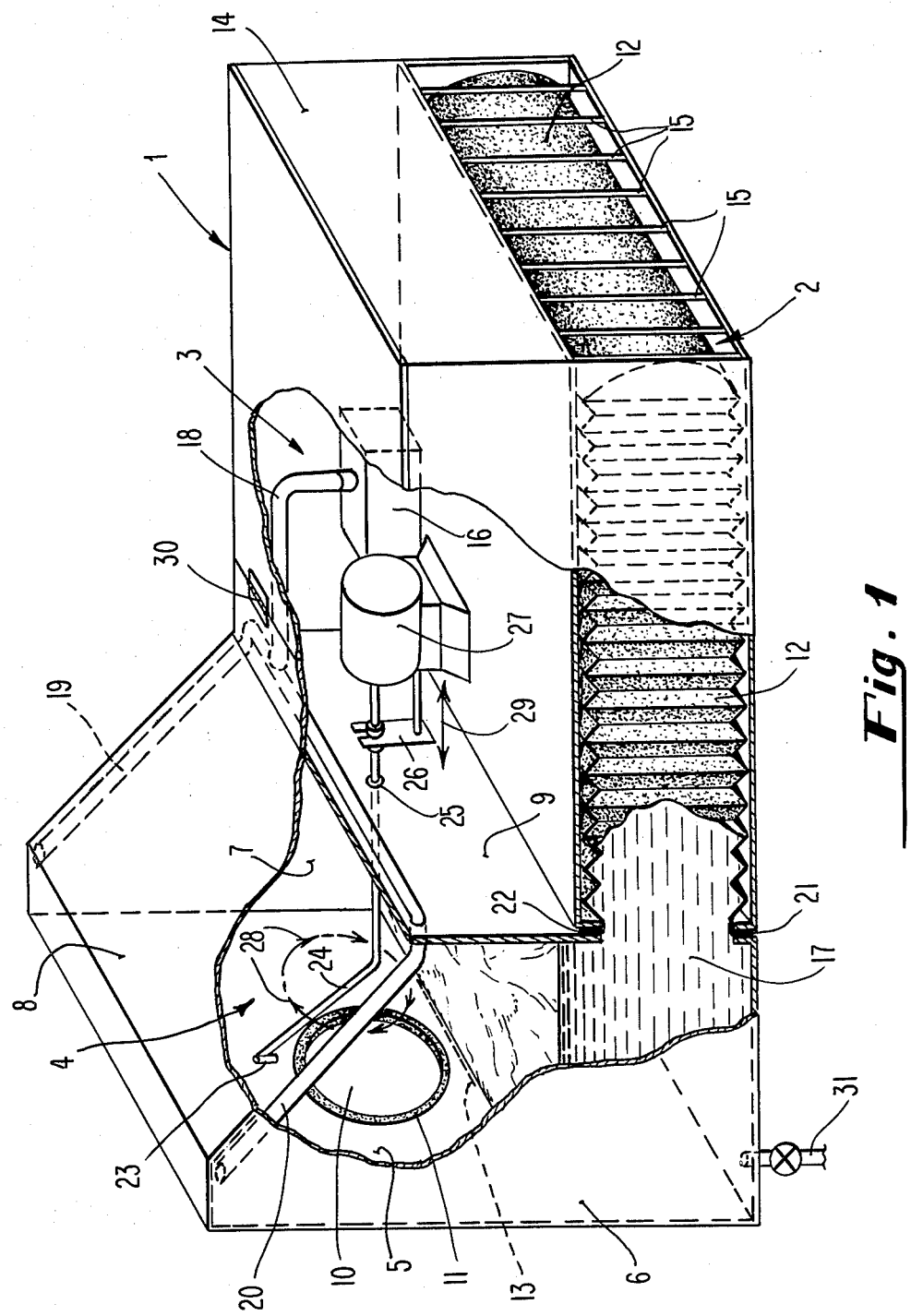
FIG. 1 is a cutaway perspective view of the ultrasonic scanner which is the subject of the present invention.

The structure of the ultrasonic scanner is illustrated in the perspective view of FIG. 1. A housing, indicated generally by reference numeral 1, comprises a collapsible bag compartment 2, an instrument compartment 3, and a water bath compartment 4. Water bath compartment 4 is defined by end panel 5, side panels 6 and 7, and overhead panel 8. Panel 9 separates water bath compartment 4 from instrument compartment 3. These panels are preferably constructed of a transparent, non-breakable material, such as Plexiglas having a thickness 0.25 inches. (Plexiglas is a registered trademark of the Rohm and Haas Co.) End panel 5 defines hole 10, which hole is lined by cushioned ring 11. The inner diameter of ring 11 is chosen to be comparable to the diameter of a breast of the woman undergoing the examination; thus rings with various inner diameters should be available.

Pleated collapsible bag 12 lies within collapsible bag compartment 2, and said bag opens directly into water bath compartment 4. Collapsible bag 12 is typically constructed of rubber or any other type of flexible and strong material. In the preferred embodiment, bag 12 can collapse as a pair of bellows, but it is understood that the bag may also be constructed without pleats, so that it may collapse like a deflated balloon. Water (or any other liquid) is poured into bag 12, until the entire bag 12 is filled, and until the water level has risen, within water bath compartment 4, to the level indicated by water level line 13 on end panel 5. Water level line 13 is located about midway between the level of the lower edge of hole 10 and the level of the top of bag 12. The volume of bag 12, in its completely filled state, must be approximately equal to the volume of that portion of the water bath compartment 4 which lies above the water level line 13, so that when bag 12 is completely collapsed, all the water within the bag will fill almost all of the space within water bath compartment 4. Protrusions 21 and 22 tend to act as catching means to prevent bag 12 from being drawn into water bath compartment 4 even when bag 12 is completely collapsed. The opening between water bath compartment 4 and collapsible bag compartment 2 may also comprise, as an additional optional feature, a plurality of bars placed across the opening, in order to prevent collapsible bag 12 from being drawn into water bath compartment 4 when bag 12 is in its collapsible state.

Water bath compartment 4 is designed to minimize the volume of the part of compartment 4 which lies above water level line 13. Such a design minimizes the required volume of collapsible bag 12. Panel 8 is removable for easy access to compartment 4 and to the equipment therein. When panel 8 is in place, a good vacuum seal can be obtained through the use of an appropriate gasket or other type of vacuum sealing means (not shown).

Located at the bottom of rear portion 14 of housing 1 is a plurality of bars 15. Bars 15 serve to retain collapsible bag 12 within collapsible bag compartment 2, while at the same time permitting external air to exert pressure on collapsible bag 12. Although the preferred embodiment illustrates bars such as 15, it is understood that any other structure which both retains bag 12 in compartment 2 and allows ambient air to exert pressure on the bag could be used. For example, a screen or grid could be used, or an irregular configuration of holes would also suffice.

Evacuation pump 16 is located within instrument compartment 3, and provides the suction needed to draw water 17 up into water bath compartment 4. Evacuation pump 16 draws air through duct 18, and tubes 19 and 20, to achieve the desired effects. The minimum vacuum needed for a full collapse of collapsible bag 12, as measured at the outlet to evacuation pump 16, is equal to the pressure of the water column in the water bath compartment 4, or approximately 30 mm Hg below the atmospheric pressure. Hence, the evacuation pump 16 must have sufficient suction power to create a vacuum of at least 30 mm Hg below atmospheric pressure, and preferably 40 mm Hg below atmospheric pressure. The pressure at the level of the breast is approximately 15 mm Hg less than that at the top of water bath compartment 4, or about 25 mm Hg below atmospheric pressure. It is also desirable for purposes of speed of the examination procedure, that pump 16 be capable of raising the water level to a point near the top of water bath compartment 4 in about 6-12 seconds. In the preferred embodiment, the volume to be evacuated is approximately 12 liters, so pump 16 should be chosen so that it can pump approximately 1-2 liter/second. Evacuation pump 16 may be controlled manually by a remote control similar to that used for a slide projector, or may be connected to a control system containing a vacuum gauge for automatic pumping to a set vacuum. As will be made clear below, the partial vacuum created by pump 16 serves two purposes: it causes water to be drawn upward and over the breast, and it holds the breast in place during the examination.

Ultrasonic scanning is accomplished by ultrasonic transducer 23 mounted on shaft 24, the shaft of which enters the water bath compartment 4 from the instrument compartment 3 through sealed bearing 25 located in panel 9. Motor 27 and shaft guide 26 hold shaft 24. Motor 27 provides both rotational motion for the shaft, as illustrated by arrows 28, and translational motion, as illustrated by arrows 29. It is understood that motor 27 is shown only by way of illustration; a solenoid or any other type of electromechanical device might be used in addition. It is seen that upon rotation of shaft 24, transducer 23 can be made to revolve around a breast (not shown in FIG. 1), and that scanning can be accomplished around a 360° arc, as indicated by arrows 28. Also, by varying the position of the shaft 24 as illustrated by arrows 29, it is possible to obtain scans of different planes of the breast, in order to carry out a complete examination.

Transducer 23 generates a brief ultrasonic pulse with a frequency in the range of 2-5 MHz. This frequency range is chosen because it offers a good compromise between resolution and attenuation; with a higher frequency, the ability to resolve small objects is improved, while with a lower frequency, the sound attenuation by the tissue is reduced, thus giving an improved sound penetration. The pulse of ultrasonic energy is generated by conventional equipment, not shown. Detection, amplification, and the display of the ultrasonic echoes are accomplished by an apparatus which is well known in the art, and this is not shown in FIG. 1 for the sake of clarity.

Although the dimensions of the apparatus are not critical, in the preferred embodiment, the apparatus is about 0.6 meters long, and about 0.4 meters high (measured from the highest point of the apparatus), and about 0.3 meters wide. The top surface of instrument compartment 3 can be opened by means of hinge 30, so that the parts within the apparatus can be readily serviced. The apparatus also comprises a valve 31 which facilitates the draining of water from the apparatus when necessary. Valve 31 need not be used, however, during the course of each test, as the water in the apparatus would need to be changed relatively infrequently. Chlorine may be added to the water for purposes of cleanliness.

FIG. 2 illustrates the position assumed by the patient 51 relative to the ultrasonic scanning apparatus described above. It is seen that the patient sits comfortably, her breast protruding through hole 10 (not shown in FIG. 2), while the examination is in progress.

The major steps of the breast cancer examination are illustrated in FIGS. 3a, 3b, and 3c. FIG. 3a is a partially schematic view of the apparatus as it might appear shortly after a breast has been inserted, but before any pumping has begun. It is seen that water 17 completely fills collapsible bag 12, and extends into water bath compartment 4, up to water level line 13 (visible only in FIG. 1) which line lies below the bottom of the breast. Bag 12 is fully extended, and lies along substantially the entire length of the collapsible bag compartment.

Next, evacuation pump 16 is actuated, causing air to be drawn into tube 20, as illustrated by air-flow arrows 36. Because of the partial vacuum produced in the upper portions of water bath compartment 4, and because of ambient air pressing at atmospheric pressure on the far end of bag 12, as illustrated by arrows 37, water is forced upward into water bath compartment 4, and bag 12 begins to collapse.

In FIG. 3c, water 17 has been drawn substantially through the entire water bath compartment 4, and water 17 completely covers the breast and lies above the highest possible position of transducer 23. Of course, the water level must never be allowed to rise to the level of the top of tube 20; water must not flow into evacuation pump 16. A simple safety valve of well-known construction, (not shown for the sake of clarity) can be used to prevent the partial vacuum in water bath compartment 4 from exceeding a given value (such as 50 mm Hg below atmospheric pressure).

When the water 17 has completely covered the breast and the transducer 23, as shown in FIG. 3c, the scanning process may be performed in the conventional manner. A series of pulses, as described above, is emitted by transducer 23, and the reflected pulses are received, amplified, and displayed on conventional apparatus (not shown). Shaft 24 is rotated to achieve 360° scans, and is also moved laterally to enable the operator of the apparatus to obtain scans of different planes of the breast. Sensing potentiometers (not shown) are used to register the position of transducer 23 and to control the electron beam in a B-scope display (also not shown). When the ultrasonic scanning is completed, the vacuum is slowly released, so that the bag 12 will once again fill with water, and thereby lower the water level in water bath compartment 4.

It should be emphasized that no membrane or other covering is needed to surround the breast during this examination. Thus, there is no medium (other than the water) which separates transducer 23 from the breast tissue, and which might unduly interfere with transmission and reflection of ultrasonic waves. Note also that the partial vacuum created in water bath compartment 4, in addition to performing the function of drawing water 17 over the breast, also has the effect of gently pulling the breast into water bath compartment 4, so that the breast effectively seals the hole 10 (not shown in FIGS. 3a-3c) to prevent the escape of water from the apparatus. The breast, being held in place by the vacuum, is therefore unlikely to move during the examination, and the results of the examination are thus made more reliable, because the ultrasonic pulses can be aimed at a stationary target.

During the examination, the patient may be seated in a comfortable position. Also, there is no need for artificial support for the breast because the buoyancy of the water will provide natural support. The breast is not deformed during the examination, as by manipulation. Also, the entire execution of the scanning procedure can be learned quickly, without extensive training.

If an air leak should be created, during a scan, between the skin and cushioned ring 11, the vacuum within water bath compartment 4 will probably prevent water from running out, because air will be sucked into the leak. In the event of a large leak, the vacuum would be released, and collapsible bag 12 would immediately fill with water, thus preventing any excessive spilling of water.

In order to keep the water in water bath compartment 4 at a temperature which is comfortable for skin contact, a heater element, not shown in the drawings, could be placed at the bottom of water bath compartment 4. The heater element could be controlled by thermostat via a temperature sensor positioned below the water level line 13. Also, a vacuum gauge for constant monitoring of the partial vacuum in water bath compartment 4 should be provided for the operator of the apparatus. Such a gauge is not shown in the drawings, but is well known in the art.

The operation of the present invention can now be concisely summarized. The apparatus is filled with water up to the water level line, and this water can be used for examining a large number of patients. A patient is then seated next to the apparatus. A skin oil or other lubricant is put on the skin around the breast, and the breast is then inserted into the cushioned hole. The evacuation pump is actuated, and after about 20 seconds, the water bath compartment is filled with water. Ultrasonic wave energy is then directed at the breast, and three or four 360° scans are performed. Unless unusual symptoms are observed, the scanning process need require only about one minute. The vacuum is then released, and in about ten seconds, the water will recede to its initial level, and the breast can be removed. Thereupon, the other breast is inserted into the hole, and the process repeated. The total time required per patient is therefore expected to be less than five minutes.

The scanning process described in this invention is easily reproducible if a record is kept of the precise amount of vacuum used during the test. This allows a reliable information base to be generated which may be very valuable for comparison with scans performed at a later time.

It is clear that the objects of the present invention have been fulfilled by the above disclosure. It is also clear that many modifications of this method and apparatus are contemplated within the scope of this disclosure. For example, although the liquid used in the illustrations above is water, any other suitable liquid could be employed. As noted earlier, the precise structure of the collapsible bag is not critical. Indeed, a piston could replace the collapsible bag, although it is preferred that no piston be used, because there will always exist a potential risk for the piston to become stuck, with a resulting spill of water when the vacuum is released. The collapsible bag, however, due to its simplicity, is very unlikely to cause malfunctions. The precise means of accomplishing the ultrasonic scanning is variable, according to methods which are well known in the art. The image may be displayed on a B-scope, or on any other suitable device, and control of the scanning plane can be accomplished manually, as by a joystick, or automatically, with the aid of a motor. The actual imaging technique can also be varied. For example, transmission scanning based on time delay spectrometry, computerized tomography based on transmission measurements, acoustical holography, or phased annular array scanning could be used in place of the pulse-echo technique. It is also possible to tilt the transducer, so as to obtain scans of tissue adjacent to the breast. These and other modifications are encompassed within the scope of this disclosure. The claims set forth below should not be deemed limited to the particular embodiments illustrated herein.

What is claimed is:

1. Apparatus for ultrasonic breast examination of a patient positioned in an upright manner comprising:
   (a) an enclosure having a hole, said hole of appropriate size to fit a breast inserted horizontally therein;
   (b) flexible means for storing fluid, said fluid-storage means being in communication with said enclosure;
   (c) means for evacuating the upper portions of said enclosure, wherein said evacuation means is of sufficient suction to draw fluid to a level near the top of said enclosure when a breast is inserted into said hole; and
   (d) ultrasonic scanning means for directing ultrasonic wave energy towards various locations in the breast.

2. The apparatus of claim 1, wherein said fluid-storage means is disposed in a chamber, said chamber having at least one opening, wherein said opening permits communication of the outside of said fluid-storage means with ambient air.

3. The apparatus of claim 2, wherein said scanning means comprises a transducer, wherein said transducer is rotatable along a 360° arc substantially concentric with said hole.

4. The apparatus of claim 3, further comprising means for varying the linear distance of said transducer from said hole, wherein said transducer may be positioned at a continuum of locations near said hole.

5. The apparatus of claim 4, wherein said fluid-storage means comprises a pleated, compressible bag.

6. The apparatus of claim 5, wherein said evacuating means comprises an evacuation pump, and at least one openended duct connected to said pump, wherein said duct terminates within the upper portion of said enclosure.

7. The apparatus of claim 6, wherein said hole is lined with a cushioned ring.

8. The apparatus of claim 7, wherein said hole extends through a side wall of said enclosure and into the upper portion of thereof.

9. Ultrasonic scanning apparatus for breast examination of a patient positioned in an upright manner, comprising:
   (a) a water bath compartment having a hole of appropriate size to accommodate a breast;
   (b) a collapsible bag compartment, comprising a collapsible, water-tight bag, said bag opening into said water bath compartment, and wherein said collapsible bag compartment has at least one opening in the vicinity of the closed end of said bag;
   (c) evacuation pump means for applying suction to the upper portion of said water bath compartment, of sufficient force to pull water out of said bag and into the upper regions of said water bath compartment, and around said breast when said breast is inserted into said hole; and
   (d) an ultrasonic transducer mounted on a rotatable and slidable member, wherein said transducer may be positioned at various locations around said breast and within the water in said water bath compartment.

10. The apparatus of claim 9, further comprising catching means for preventing said bag from entering said water bath compartment in response to suction from said pump means.

11. The apparatus of claim 10 wherein said hole is in the side of said water bath compartment for receiving said breast into said water bath compartment, said hole being located within said upper portion of said water bath compartment.

12. The apparatus of claim 11 also including a cushioned ring about said water bath compartment hole.

13. A method of ultrasonic breast examination, comprising the steps of:
   (a) partially filling a compartment with water;
   (b) inserting a breast into a hole in said compartment;
   (c) applying suction from the top of said compartment of sufficient force to draw water over said breast and towards the top of said compartment;
   (d) directing ultrasonic wave energy towards the various points on said breast; and
   (e) detecting the ultrasonic waves reflected from said breast.

14. The method of claim 13, further comprising the steps of releasing the suction applied within said compartment, and allowing the water in said compartment to recede below the level of said breast.

15. The method of claim 14, wherein said directing step comprises the steps of causing an ultrasonic transducer to revolve around said breast, and varying the location and orientation of the plane of revolution of said transducer.

16. The method of claim 13 wherein said inserting step includes inserting said breast horizontally into a hole in a side of said compartment.

17. Ultrasonic patient examining apparatus, comprising:
   (a) an fluid bath compartment having a hole through a sidewall thereof, said hole being capable of receiving a portion of said patient's body for positioning said body portion within said fluid bath compartment while said patient is positioned in an upright manner;
   (b) ultrasonic scanning means for directing ultrasonic wave energy towards said positioned body portion within said fluid bath compartment; and
   (c) means for filling said fluid bath compartment with ultrasonic transmission fluid and for contributing to a fluid seal at said compartment hole, said filling means being capable of surrounding said positioned body portion and said ultrasonic scanning means with said fluid, said positioned body portion and said ultrasonic scanning means each being thereby in direct contact with said fluid.

18. The apparatus of claim 17 wherein said fluid bath compartment hole is of a size for receiving a patient's breast; wherein said fluid bath compartment has an enclosed top; and wherein said filling means includes means for evacuating the enclosed top of said fluid bath compartment.

* * * * *